United States Patent [19]

Thompson

[11] Patent Number: 4,650,489
[45] Date of Patent: Mar. 17, 1987

[54] PROSTHETIC DEVICE FOR IMPLANTATION IN BONE

[75] Inventor: Amy Thompson, Cambridge, Mass.

[73] Assignee: Massachusetts Institute of Technology, Cambridge, Mass.

[21] Appl. No.: 824,140

[22] Filed: Jan. 30, 1986

[51] Int. Cl.⁴ .......................... A61F 2/28; A61F 2/30; A61F 2/36
[52] U.S. Cl. ........................................ 623/16; 623/18; 623/23; 128/92 R; 128/92 VP
[58] Field of Search .................. 623/16, 16 A, 18, 20, 623/22, 23; 128/92 R, 92 XP

[56] References Cited

U.S. PATENT DOCUMENTS

| | | | |
|---|---|---|---|
| 3,894,197 | 7/1975 | Mittelmeier et al. | 623/22 |
| 3,905,777 | 9/1975 | Lacroix | 29/183.5 |
| 3,938,198 | 2/1976 | Kahn et al. | 623/22 |
| 3,996,625 | 12/1976 | Noiles | 623/18 X |
| 4,051,559 | 10/1977 | Pifferi | 623/22 |
| 4,064,547 | 12/1977 | Burstein et al. | 623/23 X |
| 4,227,265 | 10/1980 | Frey | 623/16 |
| 4,259,072 | 3/1981 | Hirabayashi et al. | 433/173 |
| 4,283,799 | 8/1981 | Pratt, Jr. et al. | 623/23 |
| 4,399,814 | 8/1983 | Pratt, Jr. et al. | 128/92 |
| 4,430,761 | 2/1984 | Niederer et al. | 623/23 X |

FOREIGN PATENT DOCUMENTS

| | | | |
|---|---|---|---|
| 2247721 | 4/1974 | Fed. Rep. of Germany | 623/22 |
| 2808740 | 9/1979 | Fed. Rep. of Germany | 623/18 |

Primary Examiner—Ronald L. Frinks
Attorney, Agent, or Firm—Hamilton, Brook, Smith & Reynolds

[57] ABSTRACT

The invention resides in a prosthesis device for implantation in a human or animal bone and includes a nonperforated sheath (4) having an open end (8) and a closed end (10). A rigid core (6) extends within the sheath. A member (22) divides the cavity into two portions (14 and 16), one being filled with elastomeric material and the second portion (16), adjacent the closed end of the sheath, is a pocket of compressible fluid defined by the interior of the closed end of the sheath and the member 22.

19 Claims, 3 Drawing Figures

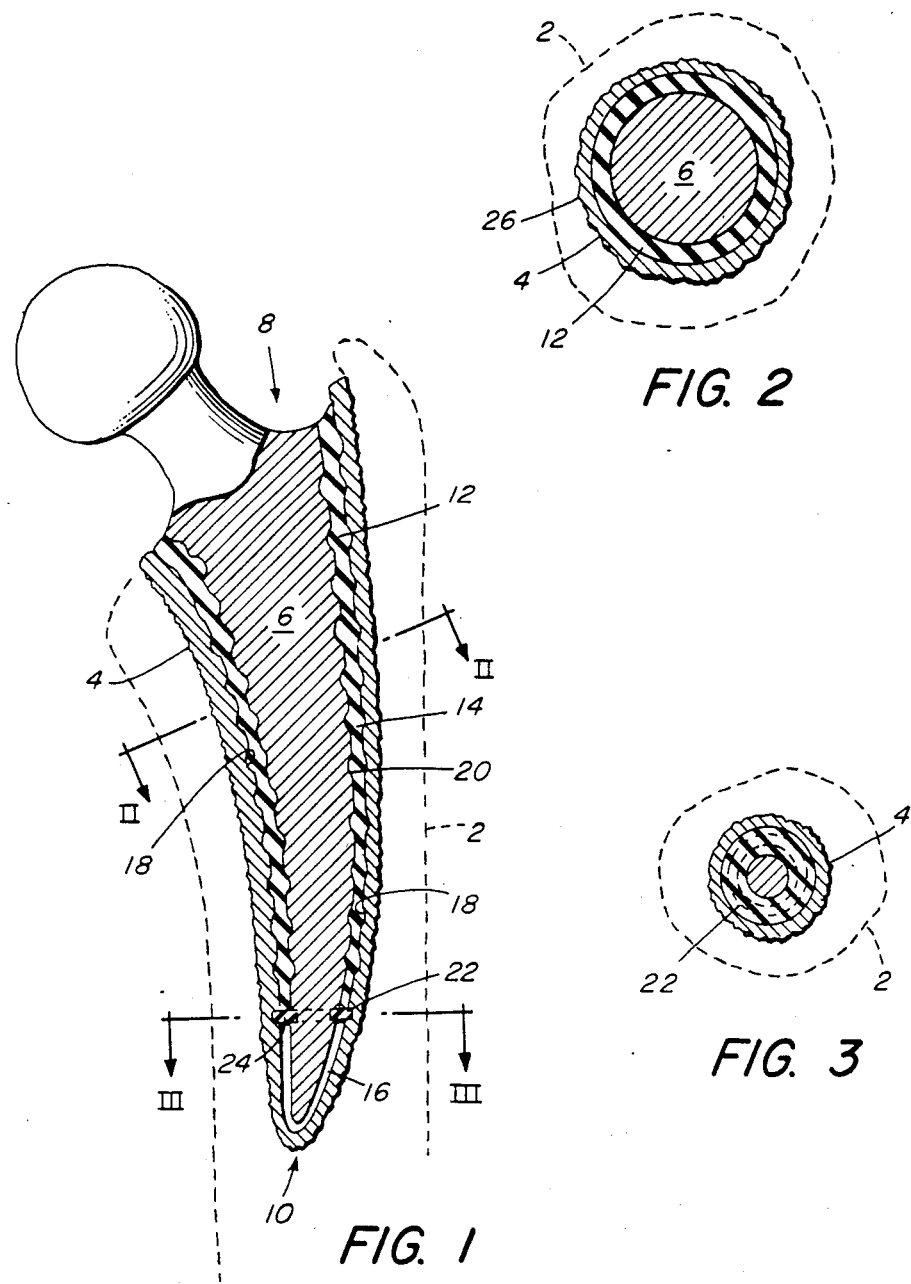

PROSTHETIC DEVICE FOR IMPLANTATION IN BONE

FIELD OF THE INVENTION

This invention relates to medical devices and more particularly to prosthetic devices for implantation in a human or animal bone.

BACKGROUND OF THE INVENTION

There are many prosthetic devices for implantation in human or animal bones. One of the more commonly used types includes a solid member which is cemented directly into a cavity in the bone. An example of this is a prosthetic device used to replace the head of a human femur. The device is generally a solid stainless steel or titanium steel curved shaft mounting a ball at one end.

A cavity is prepared in the bone as for example reaming the medullary canal in the human femur. A cement such as polymethylmethacrylate, also known as PMMA, is poured into the cavity and the prosthetic device inserted. The cement hardens within a few minutes. However, the hardening process is exothermic and the evolved heat kills the bone cells adjacent the implant. When the cells grow back, they form a fibrous layer which encapsulates the prosthesis. This layer is hard and after its formation provides poor damping properties when impact is imparted to the prosthetic device.

It has been found that the device tends to jar loose and the cement-bone interface in time breaks down. The implant then must be replaced on an average of every 5 to 10 years, and when this occurs, the old cement must be completely removed from the cavity. This tends to weaken the original bone because the fibrous bone layer must also be removed.

It is one of the objects of this invention to provide a prosthetic device which in the implantation process does not require an exothermic cement.

Another object of this invention is to provide a prosthetic device which need not be completely removed if a portion of it requires replacement or repair.

SUMMARY OF THE INVENTION

The invention resides in a prothesis device for implantation in a human or animal bone. It comprises three parts: an elongated, nonperforated sheath, a metallic ball and shaft which make up the core of the implant, and an elastomeric layer between the sheath and the core. The sheath has an open upper end and a closed lower end. The core, having a profile substantially similar to the interior of the sheath but of a smaller cross section, extends lengthwise within the sheath. At a point spaced from the closed end of the sheath is a flexible retaining and spacing member surrounding the core in position and engaging the interior of the sheath. The flexible member serves to retain the core within the sheath, spacing it from the wall of the sheath thereby producing a cavity between the core and the interior of the sheath. The flexible member also divides the cavity into a first upper portion contiguous with the open end of the sheath and a closed lower portion contiguous with the closed end of the sheath. The core terminates short of the closed end. The first upper open portion of the cavity is filled with an elastomic material and the closed lower portion with a compressible fluid, such as air.

The interior surface of the sheath and the exterior surface of the core may be provided with bumps or with indentations to better retain the elastomeric material in place after it has set. The exterior surface of the sheath is provided with minute bumps or indentations to promote the growth of bone which interdigitates with the implanted sheath. The resulting spongy bone provides better damping to impact upon the core, and hence, the sheath, than either compact bone or fibrous capsule.

The presence of the elastomeric material within the cavity provides damping to impact transmitted through the core. It reduces stress concentrations and allows some vertical displacement relative to the sheath.

The pocket of compressible fluid at the lower or closed end of the sheath enables the core to be displaced slightly vertically, i.e., lengthwise of the sheath under shock. This will occur to a greater degree than if the elastomeric material filled the entire cavity since the portion at the apex of the closed end would be subject to compression. The elastomer will deform more readily in shear than compression.

Should it become necessary to remove the core for repair or replacement, the sheath is not removed from the bone, the bony ingrowth is therefore not disturbed.

It is only necessary to remove the elastomeric material, repair or replace the core, re-insert the core, and refill the upper portion of the cavity with elastomeric material.

BRIEF DESCRIPTION OF THE DRAWINGS

FIG. 1 is a elevational view, partially in section, of a prosthetic device embodying the features of this invention.

FIG. 2 is a sectional view taken on the line II—II of FIG. 1.

FIG. 3 is a sectional view taken on the line III—III of FIG. 1.

BEST MODE OF CARRYING OUT THE INVENTION

A prosthesis device embodying the features of the invention is shown partially in cross section inserted in the medullary canal of a human femur which lacks a femoral head. It will be understood, however, that this particular prosthetic device and the location where it is implanted, is merely illustrative of the invention since other bone prosthesis of different shapes and forms intended for location elsewhere in humans or animals are within the scope of this invention.

The upper portion of a human femur lacking a femural head is designated 2. In the medullary canal within the femur is a sheath 4 within which there is located a relatively rigid core 6. The sheath is nonperforated and has an open end 8 and a closed end 10. Surrounding the core 6 and within the interior of the sheath 4 is a cavity comprising a first portion 14 contiguous with the open end 8 of the sheath and second portion 16 continguous with the closed end.

The sheath 4 and the core 6 may be made of stainless steel but preferably are made of titanium steel. The core is solid and may have the general configuration of a Charnley type prosthesis. The interior surface of the sheath includes indentations 18 (which also may be projections) and the exterior surface of the core includes indentations 20. The shape and size of the indentations will vary with the material that is used to fill the first or open portion 14 of the cavity. It will be noted that no indentations are shown in the lower or closed portion 16 of the cavity simply because they are not needed. It is within the scope of the invention, however, that the entire inner wall of the sheath and the entire surface of the core can include indentations if it is more expenditous that these elements be manufactured in that fashion.

There are indentations or minute bumps on the outer surface of the sheath, herein called irregularities, which are substantially smaller that those within the sheath and are virtually unperceptible in the drawings since they are intended for a totally different purpose. The mean diameter of the indentations is of the order of 150 microns to promote bony ingrowth.

Within the sheath is a flexible element 22 which has a number of functions and may be called by a number of names. One of the functions of the element 22 is that of a retainer ring. It is a circular ring shown as rectangular in cross section but need not necessarily so, for example, it may also be in the form of a "O" ring. It engages the inner wall of the sheath and, may if desired, fit into an annular ring 24 formed in the wall. The member 22 is flexible being made of butyl rubber or the like. Its interior diameter engages the exterior surface of the core 6. With the core 6 within the sheath 4 as shown in FIG. 1, at any given point lengthwise of the sheath, the cross section of the core is less than the cross section of the interior of the sheath at that point. Hence, the cavity 12 within the sheath and surrounding the core.

The member 22 in its function as a retainer ring serves to keep the core 6 spaced from the interior wall of the sheath. Hence, in describing this function it is called a retainer or spacer ring.

The member 22 also serves another function, that of dividing the cavity 12 into two parts: the first open upper portion 14 contiguous with the open end 8 of the sheath and the closed lower portion 16 contiguous with the closed end 10 of the sheath.

The lower portion 16 of the cavity 12 is filled with any biocompatible compressible fluid. The compressible fluid may be an inert gas or air.

The upper portion 14 of the cavity is filled with an elastomeric material, such as silicon, butyl rubber, Biomer made by the Lord Company of Erie, Pennsylvania, which is a biocompatible rubber.

The prosthetic device is implanted in the following manner. The medullary canal is prepared in the conventional manner as by reaming. Other than by conventional medical practices of making the canal antiseptic, no other material such as polymethylmethacrylate cement is placed in the cavity or around the sheath. The core, the sheath, and the element 22 are assembled as shown in FIG. 1. The complete implant comprising the sheath, the spacer members, the elastomeric filler, and the core is impacted into the cavity. If it be desired to fill the closed cavity 16 with an inert gas, this is done before assembly, otherwise, it is assembled as shown with air being trapped in the cavity 16.

The outer irregular surface of the sheath, whether it includes minute bumps or indentations provides an ideal hard surface for the regrowth of bone. In the growing process the bone interdigitates with the sheath, resulting in a cancellous or spongy bone 26 (FIG. 2), providing better damping than either compact bone or the fibrous capsule which developed through the use of the exothermal cements heretofore used.

The compressible fluid, such as air or any other selected gas in the closed cavity 16 at the closed end of the sheath, enables the core to be displaced vertically under shock. The elastomer in the upper portion of the cavity tends to yield slightly under shock on the head of the core. Were the elastomer to fill both the upper and lower portions of the cavity, resistance to deformation would be observed at the closed end of the sheath since the core would then be exerting a compressive force against the elastomer in the closed end of the sheath.

I claim:

1. A prosthesis device for implantation in a human or animal bone comprising:
    a sheath having an open end and a closed end,
    a core within the sheath,
    a cavity within the sheath, a portion of said cavity being filled with an elastomeric material,
    a divider ring within the sheath surrounding a portion of the core and spaced from the closed end,
    a pocket of compressible fluid surrounding the core and defined by the interior of the closed end of the sheath and the divider ring.

2. A prosthesis device for implantation in a human or animal bone comprising,
    a nonperforated sheath having an open end and a closed end,
    a core within the sheath exiting from the open end and terminating short of the closed end,
    a cavity within the sheath surrounding the core,
    a dividing member disposed from the closed end of the sheath and surrounding a portion of the core, the dividing member engaging the interior of the sheath into two portions, the first portion being contiguous with the open end of the sheath and the second portion contiguous with the closed end, and
    a pocket of compressible fluid located in the second portion.

3. A prosthetic device for implantation in a human or animal bone comprising:
    a sheath having an open end and a closed end,
    a core within the sheath extending from the open end and terminating short of the closed end,
    the cross section of the core at any given point lengthwise of the sheath being less than the cross section of the sheath at that point,
    a spacer member surrounding the core at a distance from the closed end and engaging the interior of the sheath to create a cavity between the core and the interior of the sheath, and
    a pocket of compressible fluid in the cavity between the spacer member and the core.

4. Prosthesis device according to claim 1 wherein there are irregularities in the exterior surface of the sheath.

5. A prosthesis device according to claim 1 wherein there are indentations in the interior surface of the sheath.

6. A prosthesis device according to claim 1 wherein there are indentations in the surface of the core.

7. A prosthetic device according to claim 2 wherein the first portion of the cavity within the sheath is filled with an elastomeric material.

8. Prosthesis device according to claim 2 wherein there are irregularities in the exterior surface of the sheath.

9. A prosthesis device according to claim 2 wherein there are indentations in the interior surface of the sheath.

10. A prosthesis device according to claim 2 wherein there are indentations in the surface of the core.

11. Prosthesis device according to claim 5 wherein the spacer member is flexible.

12. Prosthesis device according to claim 5 wherein the portion of the cavity between the spacer member and the open end of the sheath is filled with an elastomeric material.

13. Prosthesis device according to claim 5 wherein the portion of the cavity between the spacer member and the closed end of the sheath is filled with a compressible fluid.

14. Prosthesis device according to claim 5 wherein there are irregularities in the exterior surface of the sheath.

15. A prosthesis device according to claim 5 wherein there are indentations in the interior surface of the sheath.

16. A prosthesis device according to claim 5 wherein there are indentations in the surface of the core.

17. A prosthesis device according to claim 3, wherein the spacer member is flexible.

18. A prosthesis device according to claim 3 wherein the portion of the cavity between the spacer member and the open end is filled with an elastomeric material.

19. A prosthesis device according to claim 3, wherein there are indentations in the surface of the core and in the interior surface of the sheath.

* * * * *